United States Patent [19]

Plavac

[11] Patent Number: 4,680,129
[45] Date of Patent: Jul. 14, 1987

[54] MODIFIED SUCCINIMIDES (X)

[75] Inventor: Frank Plavac, Novato, Calif.

[73] Assignee: Chevron Research Company, San Francisco, Calif.

[21] Appl. No.: 820,188

[22] Filed: Jan. 17, 1986

[51] Int. Cl.$^4$ .......................................... C10M 133/16
[52] U.S. Cl. ............................ 252/51.5 A; 548/545; 548/546; 548/547
[58] Field of Search ................... 252/515 A; 548/545, 548/546, 547

[56] References Cited

U.S. PATENT DOCUMENTS

| | | | |
|---|---|---|---|
| 3,131,150 | 4/1964 | Stuart et al. | 252/51.5 A |
| 3,367,943 | 2/1968 | Miller et al. | 252/51.5 A |
| 3,373,111 | 3/1968 | LeSuer et al. | 252/51.5 |
| 4,191,537 | 3/1980 | Lewis et al. | 44/71 |
| 4,240,803 | 12/1980 | Andress, Jr. | 252/51.5 A |
| 4,401,581 | 8/1983 | Burrows et al. | 252/51.5 A |
| 4,455,243 | 6/1984 | Liston | 252/51.5 A |
| 4,482,464 | 11/1984 | Karol et al. | 252/51.5 A |
| 4,521,318 | 6/1985 | Karol | 252/51.5 A |
| 4,548,724 | 10/1985 | Karol et al. | 252/51.5 A |
| 4,579,674 | 4/1984 | Schlicht | 252/51.5 A |
| 4,608,185 | 8/1986 | Buckley | 252/51.5 A |
| 4,612,132 | 9/1986 | Wollenberg et al. | 252/51.5 A |
| 4,614,522 | 9/1986 | Buckley | 44/63 |

Primary Examiner—William R. Dixon, Jr.
Assistant Examiner—E. M. McAvoy
Attorney, Agent, or Firm—S. R. LaPaglia; R. C. Gaffney; G. F. Swiss

[57] ABSTRACT

Disclosed are additives which are useful as dispersants in marine crankcase oils, hydraulic oils, and lubricating oils. In particular, disclosed are polyamino alkenyl or alkyl succinimides wherein one or more of the nitrogen of the polyamino moiety is substituted with:

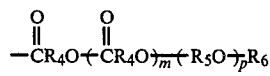

wherein $R_4$ is alkylene of from 1 to 6 carbon atoms; m is an integer of from 0 to 2; $R_5$ is alkylene of from 2 to 5 carbon atoms; p is an integer of from 1 to 100; $R_6$ is selected from the group consisting of hydrogen and hydrocarbyl of from 1 to 30 carbon atoms; and with the proviso that if m is one or two then $R_6$ is hydrogen.

16 Claims, No Drawings

MODIFIED SUCCINIMIDES (X)

BACKGROUND OF THE INVENTION

1. Field of the Invention

This invention relates to additives which are useful as dispersants and/or detergents in lubricating oils and fuels. In particular, this invention is directed toward polyamino alkenyl or alkyl succinimides wherein one or more of the nitrogens of the polyamino moiety is substituted with a substituent of the formula:

wherein $R_4$ is alkylene of from 1 to 6 carbon atoms excluding $R_4$ groups wherein

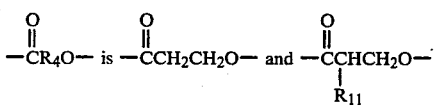

wherein $R_{11}$ is the remainder of the $R_4$ alkylene group; m is an integer of from 0 to 2; $R_5$ is alkylene of from 2 to 5 carbon atoms; p is an integer of from 1 to 100; $R_6$ is selected from the group consisting of hydrogen and hydrocarbyl of from 1 to 30 carbon atoms; and with the proviso that if m is one or two then $R_6$ is hydrogen.

The modified polyamino alkenyl or alkyl succinimides of this invention have been found to possess dispersancy and/or detergency properties when employed in a lubricating oil. These modified succinimides are also useful as detergents and/or dispersants in fuels.

2. Prior Art

Alkenyl or alkyl succinimides have been previously modified with alkylene oxides to produce poly(oxyalkylene) hydroxy derviatives thereof. These alkylene oxide-treated succinimides are taught as additives for lubricating oils (see U.S. Pat. Nos. 3,367,943 and 3,373,111). U.S. Pat. No. 4,482,464 discloses succinimides which habe been modified by treatment with a hydroxyalkylene carboxylic acid selected from glycolic acid, lactic acid, 2-hydroxymethylpropionic acid and 2,2'-bis-hydroxymethylpropionic acid. These modified succinimides of U.S. Pat. No. 4,482,464 are disclosed as lubricating oil additives. U.S. Pat. No. 4,191,537, among others, discloses hydrocarbyl capped poly(oxyalkylene) polyamino carboamates useful as dispersants and detergents in fuels and lubricating oils. However, there is no teaching in these patents, or apparently elsewhere, to modify these polyamino alkenyl or alkyl succinimides in the manner of this invention.

SUMMARY OF THE INVENTION

The present invention is directed toward a polyamino alkenyl or alkyl succinimide wherein one or more of the nitrogens of the polyamino moiety is substituted with:

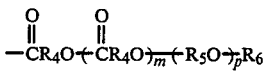

wherein $R_4$ is alkylene of from 1 to 6 carbon atoms excluding $R_4$ groups wherein

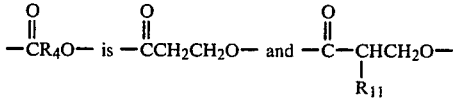

wherein $R_{11}$ is the remainder of the $R_4$ group of 1 to 6 carbon atoms; m is an integer of from 0 to 2; $R_5$ is alkylene of from 2 to 5 carbon atoms; p is an integer of from 1 to 100; $R_6$ is selected from the group consisting of hydrogen and hydrocarbyl of from 1 to 30 carbon atoms; and with the proviso that if m is one or two then $R_6$ is hydrogen.

These modified succinimides are dispersants and/or detergents for use in fuels or oils. Thus, the present invention also relates to a lubricating oil composition comprising a major amount of an oil of lubricating viscosity and an amount of a modified polyamino alkenyl or alkyl succinimide sufficient to provide dispersancy and/or detergency.

Another composition aspect of this invention is a fuel composition comprising a major portion of a hydrocarbon boiling in a gasoline or diesel range and an amount of a modified alkenly or alkyl succinimide sufficient to provide dispersancy and/or detergency.

In general, the alkenyl or alkyl group of the polyamino alkenyl or alkyl succinimide is from 10 to 300 carbon atoms. While the modified succinimides of this invention possess good detergency properties even for alkenyl or alkyl groups of less than 20 carbon atoms, dispersancy is enhanced when the alkenyl or alkyl group is at least 20 carbon atoms. Accordingly, in a preferred embodiment the alkenyl or alkyl group of the succinimide is at least 20 carbon atoms (i.e., the alkenyl or alkyl group is from 20 to 300 carbon atoms).

In other preferred embodiments of this invention, $R_4$ is preferably alkylene of from 1 to 4 carbon atoms and more preferably, alkylene of 1 carbon atom. In the above preferred embodiments, $R_4$ is not $-CH_2CH_2-$ or

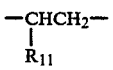

wherein $R_{11}$ if as defined above. $R_4$ groups of this nature are subject to decomposition and accordingly are not within the scope of this invention.

Preferably, m is zero.

Preferably, $R_5$ is alkylene of 2 to 4 carbon atoms. Preferably, p is an integer of from 1 to 30; more preferably, p is an integer of from 1 to 20; and most preferably, p is an integer of from 1 to 10.

Preferably, $R_6$ is hydrogen or hydrocarbyl of from 1 to 20 carbon atoms. More preferably, $R_6$ is hydrogen or hydrocarbonyl of from 1 to 10 carbon atoms and most preferably, $R_6$ is hydrogen.

Hydrocarbyl, as used in describing the $R_6$ group, denotes an organic radical composed of carbon and hydrogen which may be aliphatic, alicyclic, aromatic or combinations thereof, e.g., aralkyl. Preferably, the hydrocarbyl group will be relativey free of aliphatic unsaturation, i.e., ethylenic and acetylenic, particularly acetylenic unsaturation.

Alkylene, as used in describing the $R_4$ and $R_5$ components, denotes both straight- and branched-chain alkylene groups, i.e., 1,3-propylene, (—CH₂CH₂CH₂—); 1,2-propylene,

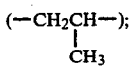

1,4-butylene, (—CH₂CH₂CH₂CH₂—); 2,3-butylene,

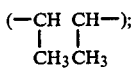

and the like. Suitable alkylene $R_4$ groups are methylene, (—CH₂—); ethylene, (—CH₂CH₂—); 1,3-propylene, (—CH₂CH₂CH₂CH₂—); 1,2-propylene,

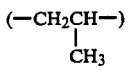

and the like.

DETAILED DESCRIPTION OF THE INVENTION

The modified polyamino alkenyl or alkyl succinimides of this invention are prepared from a polyamino alkenyl or alkyl succinimide. In turn, these materials are prepared by reacting an alkenyl or alkyl succinic anhydride with a polyamine as shown below:

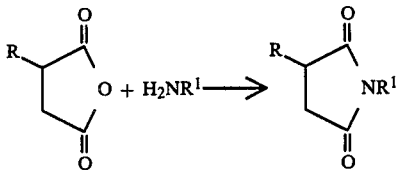

wherein R is an alkenyl or alkyl group of from 10 to 300 carbon atoms; and $R^1$ is the remainder of the polyamino moiety.

These alkenyl or alkyl succinimides that can be used herein are disclosed in numerous references and are well known in the art. Certain fundamental types of succinimides and related materials encompassed by the term of art "succinimide" are taught in U.S. Pat. Nos. 2,992,708; 3,018,291; 3,024,237; 3,100,673; 3,219,666; 3,172,892; and 3,272,746, the disclosures of which are hereby incorporated by reference. The term "succinimide" is understood in the art to include many of the amide, imide and amidine species which are also formed by this reaction. The predominant product however is succinimide and this term has been generally accepted as meaning the product of the reaction of an alkenyl substituted succinic acid or anhydride with a polyamine as shown in the reaction above. As used herein, included within this term are the alkenyl or alkyl mono-, bis-succinimides and other higher analogs.

A(1) Succinic Anhydride

The preparation of the alkenyl-substituted succinic anhydride by reaction with a polyolefin and maleic anhydride has been described, e.g., U.S. Pat. Nos. 3,018,250 and 3,024,195. Such methods include the thermal reaction of the polyolefin with maleic anhydride and the reaction of a halogenated polyolefin, such as a chlorinated polyolefin, with maleic anhydride. Reduction of the alkenyl-substituted succinic anhydride yields the corresponding alkyl derivative. Alternatively, the alkenyl substituted succinic anhydride may be prepared as described in U.S. Pat. Nos. 4,388,471 and 4,450,281 which are totally incorporated herein by reference.

Polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of 2 or more such olefins such as copolymers of: ethylene and propylene, butylene, and isobutylene, etc. Other copolymers include those in which a minor amount of the copolymer monomers, e.g., 1 to 20 mole percent is a $C_4$ to $C_8$ nonconjugated diolefin, e.g., a copolymer of isobutylene and butadiene or a copolymer of ethylene, propylene and 1,4-hexadiene, etc.

The polyolefin polymer, represented in FIG. 1 as R, usually contains from about 10 to 300 carbon atoms, although preferably 20 to 300 carbon atoms. Other preferred embodiments include 12 to 100 carbon atoms and more preferably 20 to 100 carbon atoms.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. Thse polybutenes are readily available commercial materials well known to those skilled in the art. Disclosures thereof will be found, for example, in U.S. Pat. Nos. 3,215,707; 3,231,587; 3,515,669; and 3,579,450, as well as U.S. Pat. No. 3,912,764. The above are incorporated by reference for their disclosures of suitable polybutenes.

In addition to the reaction of a polyolefin with maleic anhydride, many other alkylating hydrocarbons may likewise be used with maleic anhydride to produce alkenyl succinic anhydride. Other suitable alkylating hydrocarbons include cyclic, linear, brached and internal or alpha olefins with molecular weights in the range 100–4,500 or more with molecular weights in the range of 200–2,000 being more preferred. For example, alpha olefins obtained from the thermal cracking of paraffin wax. Generally, these olefins range from 5–20 carbon atoms in length. Another source of alpha olefins is the ethylene growth process which gives even number carbon olefins. Another source of olefins is by the dimerization of alpha olefins over an appropriate catalyst such as the well known Ziegler catalyst. Internal olefins are easily obtained by the isomerization of alpha olefins over a suitable catalyst such as silica.

A(2) Polyamine

The polyamine employed to prepare the polyamino alkenyl or alkyl succinimides is preferably a polyamine having from 2 to about 12 amine nitrogen atoms and from 2 to about 40 carbon atoms. The polyamine is reacted with an alkenyl or alkyl succinic anhydride to produce the polyamino alkenyl or alkyl succinimide, employed in this invention. The polyamine is so selected so as to provide at least one basic amine per succinimide. The polyamine preferably has a carbon-to-nitrogen ratio of from about 1:1 to about 10:1.

Since the reaction to form the modified polyamino alkenyl or alkyl succinimides of this invention is believed to efficiently proceed through a primary or secondary amine, at least one of the basic amine nitrogens of the polyamine moiety should be a primary or secondary amine.

The polyamino portion of the polyamino alkenyl or alkyl succinimide may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms.

At least one of the substituents of one of the amines of the polyamino moiety is hydrogen, e.g., at least one of the basic nitrogens is a primary or secondary amino nitrogen atom.

Hydrocarbyl, as used in describing the polyamine components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-[2-(2-ethoxyethoxy)ethoxy]ethyl, 3,6,9,12-tetraoxatetradecyl, 2-(2-ethoxyethoxy)hexyl, etc. The acyl groups of the aforementioned (C) substituents are such as propionyl, acetyl, etc. The more preferred substituents are hydrogen, $C_1$–$C_6$ alkyls, and $C_1$–$C_6$ hydroxyalkyl.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and polysubstituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethylpropylene, trimethylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydrocarbyl-substituted polyamines. Among the polyalkylene polyamines, those containing 2–12 amine nitrogen atoms and 2–24 carbon atoms are especially preferred, and the $C_2$–$C_5$ alkylene polyamines are most preferred, in particular, the lower polyalkylene polyamines, e.g., ethylene diamine, dipropylene triamine, etc.

The polyamine component also may contain heterocyclic polyamines, heterocyclic substituted amines and substituted heterocyclic compounds, wherein the heterocycle comprises one or more 5–6 membered rings containing oxygen and/or nitrogen. Such heterocycles may be saturated or unsaturated and substituted with groups selected from the aforementioned (A), (B), (C) and (D). The heterocycles are examplified by piperazines, such as 2-methylpiperazine, 1,2-bis-(N-piperazinyl)ethane, and N,N'-bis(N-piperazinyl)piperazine, 2-methylimidazoline, 3-aminopiperidine, 2-aminopyridine, 2-(3-aminoethyl)-3-pyrroline, 3-aminopyrrolidine, N-(3-aminopropyl)morpholine, etc. Among the heterocyclic compounds, the piperazines are preferred.

Typical polyamines that can be used to form the compounds of this invention include the following: ethylene diamine, 1,2-propylene diamine, 1,3-propylene diamine, diethylene triamine, triethylene tetramine, hexamethylene diamine, tetraethylene pentamine, methylaminopropylene diamine, N-(betaaminoethyl)piperazine, N,N'-di(betaaminoethyl)piperazine, N,N'-di(beta-aminoethyl)imidazolidone-2, N(beta-cyanoethyl)ethane-1,2-diamine, 1,3,6,9-tetraaminooctadecane, 1,3,6-triamino-9-oxadecane, N-methyl-1,2-propanediamine, 2-(2-aminoethylamino)-ethanol.

Another group of suitable polyamines are the propyleneamines, (bisaminopropylethylenediamines). Propyleneamines are prepared by the reaction of acrylonitrile with an ethyleneamine, for example, an ethyleneamine having the formula $H_2N(CH_2CH_2NH)_ZH$ wherein Z is an integer from 1 to 5, followed by hydrogenation of the resultant intermediate. Thus, the product prepared from ethylene diamine and acrylonitrile would be $H_2N(CH_2)_3NH(CH_2)_2NH(CH_2)_3NH_2$.

In many instances the polyamine used as a reactant in the production of succinimides of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetraamine, substituted piperazines and pentaethylene hexamine, but the composition will be largely tetraethylene pentamine and the empirical formula of the total amine composition will closely approximate that of tetraethylene pentamine. Finally, in preparing the succinimide for use in this invention, where the various nitrogen atoms of the polyamine are not geometrically equivalent, several substitutional isomers are possible and are encompassed within the final product. Methods of preparation of polyamines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volumes 2, pp. 99–116.

The reaction of a polyamine with an alkenyl or alkyl succinic anhydride to produce the polyamino alkenyl or alkyl succinimides is well known in the art and is disclosed in U.S. Pat. Nos. 2,992,708; 3,018,291; 3,024,237; 3,100,673; 3,219,666; 3,172,892 and 3,272,746. The above are incorporated herein by reference for their disclosures of preparing alkenyl or alkyl succinimides.

As noted above, the term "polyamino alkenyl or alkyl succinimide" refers to both polyamino alkenyl or alkyl mono- or bis-succinimides and to the higher analogs of polyamino alkenyl or alkyl poly succinimides. Preparation of the bis- and higher analogs may be accomplished by controlling the molar ratio of the reagents. For example, a product comprising predominantly mono- or bis-succinimide can be prepared by controlling the molar ratios of the polyamine and succinic anhydride. Thus, if one mole of polyamine is reacted with one mole of an alkenyl or alkyl substituted succinic anhydride, a predominantly monosuccinimide product will be prepared. If two moles of an alkenyl or alkyl substituted succinic anhydride are reacted per mole of polyamine, a bis-succinimide is prepared. Higher analogs may likewise be prepared.

A particularly preferred class of polyamino alkenyl or alkyl succinimides employed in the instant invention may be represented by Formula II:

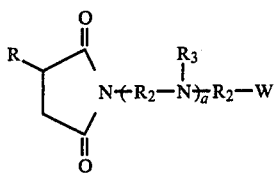

II wherein R is alkenyl or alkyl of from 10 to 300 carbon atoms; $R_2$ is alkylene of 2 to 10 carbon atoms; $R_3$ is hydrogen, lower alkyl or lower hydroxy alkyl; a is an integer from 0 to 10; and W is $-NH_2$ or represents a group of Formula III:

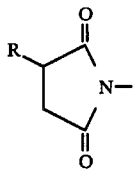

wherein R is alkenyl or alkyl of from 10 to 300 carbon atoms; with the proviso that when W is the group of Formula III above, then a is not zero and at least one of $R_3$ is hydrogen.

As indicated above, the polyamine employed in preparing the succinimide is often a mixture of different compounds having an average composition indicated as the Formula II. Accordingly, in Formula II each value of $R_2$ and $R_3$ may be the same as or different from other $R_2$ and $R_3$.

Preferably R is alkenyl or alkyl is preferably 20 to 300 carbon atoms. In another preferred embodiment, R is preferably 12 to 100 carbon atoms and more preferably 20 to 100 carbon atoms.

Preferably, $R_2$ is alkylene of 2 to 6 carbon atoms and most preferably is either ethylene or propylene.

Preferably, $R_3$ is hydrogen or lower alkyl.

Preferably, a is an integer from 1 to 6.

In Formula II, the polyamino alkenyl or alkyl succinimides may be conveniently viewed as being composed of three moieties that is the alkenyl or alkyl moiety R, the succinimide moiety represented by the formula:

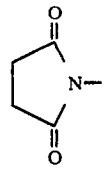

and the polyamino moiety represented by the group

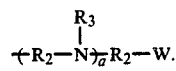

The preferred alkylene polyamines employed in this reaction are generally represented by the formula:

wherein $R_2$ is an alkylene moiety of 2 to 10 carbon atoms and a is an integer from about 0 to 10. However, the preparation of these alkylene polyamines do not produce a single compound and cyclic heterocycles, such as piperazine, may be included to some extent in the alkylene diamines.

B. MODIFIED POLYAMINO ALKENYL OR ALKYL SUCCINIMIDES

The preparation of the modified polyamino alkenyl or alkyl succinimides of this invention can be accomplished by several synthetic routes. For example, hydroxy-terminated products, i.e., $R_6 = H$ can be prepared by first reacting the polyamino alkenyl or alkyl succinimide, IV, with a hydroxy aliphatic carboxylic acid, V, under acylating conditions to yield a hydroxy aliphatic amide, VI, and secondly reacting this hydroxy aliphatic amide, VI, with an alkylene oxide, VII, under polymerization conditions as shown in reactions (1) and (2) below:

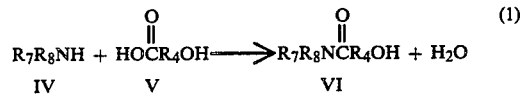

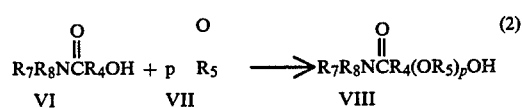

wherein $R_4$, $R_5$ and p are as defined above and $R_7R_8$ form the remainder of the polyamino alkenyl or alkyl succinimide while NH represents a primary or secondary amino group of the polyamino moiety of the polyamino alkenyl or alkyl succinimide.

Reaction (1) is a conventional acylation reaction which is well known in the art. See, for instance, U.S. Pat. No. 4,482,464 which is incorporated herein for its teaching of the preparation of hydroxy aliphatic amides of hydrocarbyl succinimides.

Reaction (1) is conducted by contacting the polyamino alkenyl or alkyl succinimide, IV, with a hydroxy aliphatic carboxylic acid, V. The reaction is conducted at a temperature sufficient to cause reaction of the hydroxy aliphatic carboxylic acid with a primary or secondary amino group of the polyamino alkenyl or alkyl succinimide. In particular, reaction temperatures of from 50° C. to 250° C. are preferred with temperatures of from 100° C. to 200° C. being most preferred.

The reaction can be conducted neat or in a suitable inert diluent. Suitable diluents include toluene, xylene, oil and the like. When a diluent is employed, it is preferably inert to the reactants and products formed and is generally used in an amount sufficient to insure efficient stirring.

Water, which can be present in the polyamino alkenyl or alkyl succinimide and/or the hydroxy aliphatic carboxylic acid, may be removed from the reaction system either before or during the course of the reaction via azeotroping or distillation. Removal of the water during the reaction is preferred because water formed during the course of reaction (1) is also removed. After reaction completion, the system can be stripped at elevated temperatures an reduced pressures to remove any volatile components which may be present in the product. The reaction is generally complete from within 1 to 24 hours. The hydroxy aliphatic amide, VI, may be further isolated by conventional techniques, such as chromatography, filtration and the like, or may be used in reaction (2) without further isolation and/or purification.

In reaction (1) above, molar ratios of hydroxy aliphatic carboxylic acid to the basic amine nitrogen of the polyamino alkenyl or alkyl succinimide are generally in the range of from about 0.3:1 to about 3:1 although preferably 0.5:1 to about 1:1 and more preferably 0.7:1 to 1:1.

As noted above, the polyamines employed to prepare the polyamino alkenyl or alkyl succinimides contan tertiary amines which may account for as much as 30% of the basic nitrogen content. Although Applicant does not want to be limited to any theory, it is believed that these tertiary amines, although basic, are not reactive with the hydroxy aliphatic carboxylic acid. Accordingly, a molar ratio of hydroxy aliphatic carboxylic acid to the basic amine nitrogen of the polyamino alkenyl or alkyl succinimide of from about 0.7:1 to about 1:1 is sufficient to convert all of the primary and secondary amine groups of the polyamino alkenyl or alkyl succinimide to hydroxy aliphatic amides. Excess glycolic acid can, under the conditions of reaction (1), react with the hydroxy aliphatic amides to form esters which are within the scope of invention as shown in reaction (1a):

(1a)

wherein $R_4$, $R_7$, $R_8$, and m are as defined above.

The hydroxy aliphatic acids, V, are either commercially available or can be prepared by art recognized techniques.

Reaction (2) is conducted by the addition of lower alkylene oxides, VII, such as oxirane, ethylene oxide, propylene oxide, the butylene oxides, or the pentylene oxides to the hydroxy compound

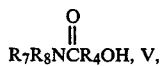

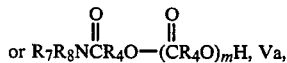

under polymerization conditions, wherein $R_7R_8$ and $R_4$ and m are as defined above.

In the polymerization reaction a single type of alkylene oxide may be employed, e.g., propylene oxide, in which case the product is a homopolymer, e.g., a poly(oxypropylene)propanol. However, copolymers are equally satisfactory and random copolymers are readily prepared by containing the hydroxyl-containing compound, V, with a mixture of alkylene oxides, such as a mixture of propylene and butylene oxides. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxides are copolymerized with other oxides, the higher reaction rate of ethylene oxide makes the preparation of random copolymers difficult. In either case, block copolymers can be prepared. Block copolymers are prepared by contacting the hydroxyl-containing compound, V, with first one alkylene oxide, then the others in any order, or repetitively, under polymerization conditions. A particular block copolymer is represented by a polymer prepared by polymerizing propylene oxide on a suitable hydroxy compound, V, to form a poly(oxypropylene) alcohol and then polymerizing butylene oxide on the poly(oxypropylene) alcohol.

In general, the poly(oxyalkylene)polymers are mixture of compounds that differ in polymer chain length. However, their properties closely approximate those of the polymer represented by the average composition and molecular weight.

The poly(oxyalkylene) group is composed of oxyalkylene units containing from 2 to about 5 carbon atoms. Preferably, the oxyalkylene units contain from 2 to 4 carbon atoms. Each poly(oxyalkylene) polymer contains from 1 to 100 oxyalkylene units, preferably 1 to about 30 oxyalkylene units, most preferably about 1 to 10 units. In general, the oxyalkylene units may be branched or unbranched. The structures of the $C_3$–$C_5$ oxyalkylene units are any of the isomeric structures well known to the organic chemist, e.g., n-propylene, —$CH_2CH_2CH_2$—; isopropylene, —$C(CH_3)CH_2$—; n-butylene, —$CH_2CH_2CH_2CH_2$—; sec.-butylene, —$CH(CH_2CH_3)CH_2$—; tert.-butylene, —$C(CH_3)_2CH_2$—; disec.-butylene, —$CH(CH_3)CH(CH_3)$—; isobutylene, —$CH_2CH(CH_3)CH_2$—; etc. The preferred poly(oxyalkylene) compounds are composed of from 1 to about 30 oxyalkylene units, more preferably about 1 to 20 oxyalkylene units and most preferably 1 to about 10 such units.

If molar changes of hydroxy aliphatic carboxylic acid, V, to the basic amine nitrogen of the polyamino alkenyl or alkyl succinimide are in the range of less than 0.7:1, the resulting aliphatic amide derivative, VI, will contain primary or secondary amino groups which will also react with alkylene oxide, VII, in reaction (2) converting these groups to hydroxy poly(oxyalkylene)amine derivatives. These modified polyamine alkenyl or alkyl succinimides are characterized by having one or more of the nitrogens of the polyamino moiety substituted with a substituent of the formula:

wherein $R_4$, $R_5$, and p are as defined above and further having one or more of the nitrogens of the polyamino moiety substituted with a substituent of the formula —$R_5O)_pH$ wherein $R_5$ and p are as defined above.

As used herein, the term "molar charge of hydroxy aliphatic carboxylic acid (or hydroxy poly(oxyalkylene)carboxylic acid) to the basic nitrogen of a polyamino alkenyl or alkylsuccinimide" means that the molar charge of hydroxy aliphatic carboxylic acid employed in the reaction is based upon the theoretical number of basic nitrogens contained in the succinimide. Thus, when 1 equivalent of triethylene tetraamine (TETA) is reacted with an equivalent of succinic anhydride, the resulting monosuccinimide will theoretically contain 3 basic nitrogens. Accordingly, a molar charge of 1 would require that a mole of hydroxy aliphatic carboxylic acid be added for each basic nitrogen or in this case 3 moles of hydroxy aliphatic carboxylic acid for each mole of monosuccinimide prepared from TETA.

In an alternative method for preparing the hydroxy-terminated products, wherein m is zero and $R_6$ is H, the hydroxy aliphatic carboxylic acid is first converted to its disodium salt (dilithium or dipotassium salts are also contemplated), followed by polymerization of this disodium salt with alkylene oxide, VII. The resulting poly(oxyalkylene) derivative, X, is then employed to acylate a primary or secondary amine of the polyamino moiety of the polyamino alkenyl or alkyl succinimide as shown in reactions (3), (4) and (5) below:

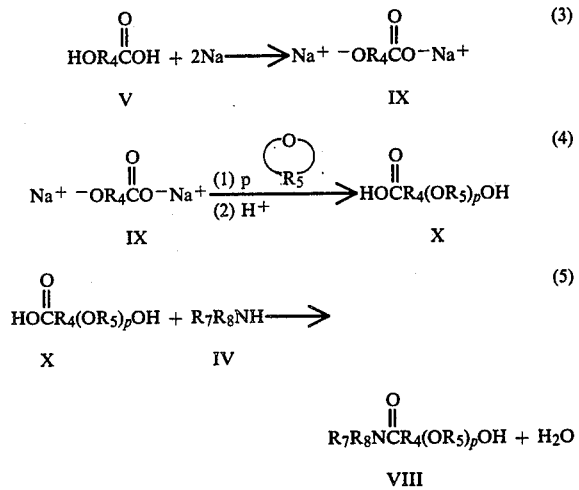

wherein $R_4$, $R_5$, $R_7$, $R_8$ and p are as described above.

Reaction (3) is a conventional reaction to form the desalt. The reaction comprises contacting 2 equivalents of metallic sodium, or alternatively, a reagent, such as sodium t-butoxide or sodium hydride (potassium and lithium are also equivalent), with the hydroxy aliphatic carboxylic acid, V. The resulting desalt, IX, can be isolated by conventional techniques, but is preferably employed in reaction (4) without purification and/or isolation.

Reaction (4) is conducted by the addition of lower alkylene oxides, VII, such as oxirane, ethylene oxide, propylene oxide, the butylene oxides, or the pentylene oxide to the desalt, IX, under polymerization conditions.

In the polymerization reaction a single type of alkylene oxide may be employed, e.g., propylene oxide, in which case the product is a homopolymer, e.g., a poly-(oxypropylene)propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene)polymers for the practice of the present invention. Random polymers are more easily prepared when the reactivities of the oxides are relatively equal. In certain cases, when ethylene oxides is copolymerized with other oxides, the higher reaction rate of ethylene oxide makes the preparation of random copolymers difficult. In either case, block copolymers can be prepared. Block copolymers are prepared by contacting the hydroxyl-containing compound with first one alkylene oxide, then the others in any order, or repetitively, under polymerization conditions. A particular block copolymer is represented by a polymer prepared by polymerizing propylene oxide on a suitable monohydroxy compound to form a poly(oxypropylene) alcohol and then polymerizing butylene oxide on the poly(oxypropylene) alcohol.

In general, the poly(oxyalkylene) polymers are mixtures of compounds that differ in polymer chain length. However, their properties closely approximate those of the polymer represented by the average composition and molecular weight.

After polymerization, the reaction solution is washed with an aqueous acidic solution so as to neutralilze the resulting product.

Reaction (5) is a conventional acylation reaction which is well known in the art. Reaction (5) is conducted by contacting the polyamino alkenyl or alkyl succinimide, IV, with the acid, X. The reaction is conducted at a temperature sufficient to cause reaction of the acid with a primary or secondary amino group of the polyamino alkenyl or alkyl succinimide. In particular, reaction temperatures of from 50° C. to 250° C. are preferred with temperatures of from 100° C. to 200° C. being most preferred.

The reaction can be conducted neat or in a suitable inert diluent. Suitable diluents include toluene, xylene, oil and the like. When a diluent is employed, it is preferably inert to the reactants and products formed and is generally used in an amount sufficient to insure efficient stirring.

Water, which can be present in the polyamino alkenyl or alkyl succinimide, IV, and or acid, X, may be removed from the reaction system either before or during the course of the reaction via azeotroping or distillation. Removal of the water during the course of the reaction is preferred because water formed during the course of reaction (5) is also removed. After reaction completion, the system can be stripped at elevated temperatures and reduced pressures to remove any volatile components which may be present in the product. The reaction is generally complete from within 1 to 24 hours. The amide, VIII, may be further isolated by conventional techniques, such as chromatography, filtration and the like.

Molar ratios of hydroxy poly(oxyalkylene) carboxylic acid, X, to the basic amine nitrogen of the polyamino alkenyl or alkyl succinimide are generally in the range of from about 0.3:1 to about 1:1 although preferably 0.5:1 to about 1:1 and more preferably 0.7:1 to 1:1.

In still another alternative method for preparing the hydroxy-terminated products, i.e., $R_6$=H, of this invention, the hydroxy aliphatic amide, VI, prepared in reaction (1) is reacted with a cyclic carbonate of the Formula XI:

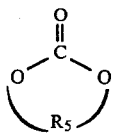   XI wherein $R_5$ is as defined above. The cyclic carbonates, XI, react with the terminal hydroxy group of the hydroxy aliphatic amide to form a poly(oxyalkylene) derivative thereof with the concomitant elimination of $CO_2$ as shown in reaction (6) below:

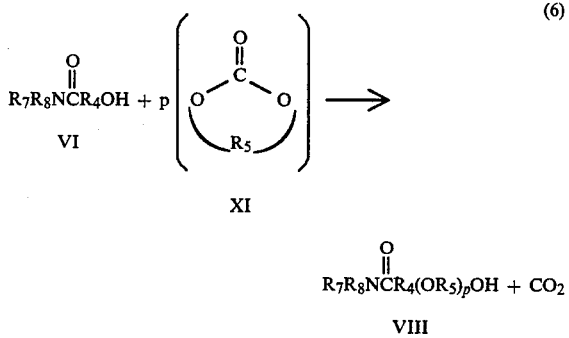

(6)

wherein $R_4$, $R_5$, $R_7$, $R_8$ and p are as defined above.

The reaction is conducted by combining the hydroxy aliphatic amide, VI, with the cyclic carbonate at a temperature sufficient to cause reaction of the cyclic carbonate with the hydroxy group of the hydroxy aliphatic amide. In particular, reaction temperatures of from about 0° to about 250° C. are preferred with temperatures of from 100° C. to 250° C. being most preferred.

The reaction may be conducted neat—that is, both the hydroxy aliphatic amide and the cyclic carbonate are combined in the proper ratio, either alone or in the presence of a catalyst, such as acidic, basic or Lewis acid catalyst, and then stirred at the reaction temperature. Examples of suitable catalysts include, for instance, boron trifluoride, alkane sulfonic acid, alkali or alkaline carbonate.

Alternatively, the reaction may be conducted in a diluent. For example, the reactants may be combined in a solvent such as toluene, xylene, oil or the like, and then stirred at the reaction temperature. After reaction completion, volatile components may be stripped off. When a diluent is employed, it is preferably inert to the reactants and products formed and is generally used in an amount sufficient to insure efficient stirring.

Water, which can be present in the dispersant, may be removed from the reaction system either before or during the course of the reaction via azeotroping or distillation. After reaction completion, the system can be stripped at elevated temperatures (100° C. to 250° C.) and reduced pressure to remove any volatile components which may be present in the product.

Mole ratios of the cyclic carbonate to the hydroxy group of the hydroxy aliphatic amide derivative of the polyamino alkenyl or alkyl succinimide employed in the process of this invention are generally in the range of from about 1:1 to about 100:1, although preferably from about 1:1 to about 30:1 and most preferably 1:1 to 10:1.

The reaction is generally complete from within 0.5 to 10 hours.

Cyclic carbonates of Formula XI are either commercially available or are readily prepared by art recognized techniques. For example, reaction of phosgene with a suitable alpha alkane diol or an alkan-1,3-diol yields a carbonate for use within the scope of this invention. See, for instance, U.S. Pat. No. 4,115,206 which is incorporated herein by reference for its teaching of the preparation of cyclic carbonates.

Likewise, the cyclic carbonates useful for this invention may be prepared by transesterification of a suitable alpha alkane diol or an alkan-1,3-diol with, e.g., diethyl carbonate under transesterification conditions. See, for instance, U.S. Pat. Nos. 4,384,115 and 4,423,205 which are incorporated herein by reference for their teaching of the preparation of cyclic carbonates.

As used herein, the term "alpha alkane diol" means an alkane group having two hydroxyl substituents wherein the hydroxyl substituents are on adjacent carbons to each other. Examples of alpha alkane diols include 1,2-propanediol, 2,3-butanediol and the like.

The term "alkan-1,3-diol" means an alkane group having two hydroxyl substituents wherein the hydroxyl substituents are beta substituted. That is, there is a methylene or a substituted methylene moiety between the hydroxyl-substituted carbons. Examples of alkan-1,3-diols include propan-1,3-diol, pentan-2,4-diol and the like.

Suitable cyclic carbonates include ethylene carbonate and propylene carbonate.

In reaction (6) above, it is contemplated that the poly(oxyalkylene) moiety of the product VIII can contain some acyclic carbonate linkages, i.e.,

These carbonate linkages do not adversely affect product VIII and are intended to be included within the scope of this invention.

If molar charges of hydroxy aliphatic carboxylic acid, V, to the basic amine nitrogen of the polyamino alkenyl or alkyl succinimide are in the range of less than 0.7:1, the resulting hydroxy aliphatic amide derivative, VI, will contain primary or secondary amine groups which will also react with cyclic carbonate, XI, in reaction (6). See, for instance, U.S. Ser. No. 722,939 which is incorporated herein for its teaching of the reaction of cyclic carbonates with polyamino alkenyl or alkyl succinimides.

Accordingly, a process aspect of this invention consists of a process for modifying a polyamino alkenyl or alkyl succinimide which comprises:

(a) contacting at a temperature sufficient to cause reaction a hydroxy aliphatic carboxylic acid of the formula $$\overset{O}{\underset{\|}{HOCR_4OH}}$$

wherein $R_4$ is alkylene of from 1 to 6 carbon atoms, with a polyamino alkenyl or alkyl succinimide wherein the molar charge of hydroxy aliphatic carboxylic acid to the basic nitrogen of the polyamino alkenyl or alkyl succinimide is from about 0.3:1 to 1:1; and (b) contacting at a temperature sufficient to cause reaction the product of (a) above with a cyclic carbonate of the formula

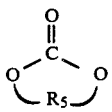

wherein $R_5$ is alkylene of 2 to 5 carbon atoms; wherein the molar charge of the cyclic carbonate to the hydroxy group of the hydroxy aliphatic amide derivative is from about 1:1 to about 100:1. with the proviso that $R_4$ is not $-CH_2CH_2-$ or

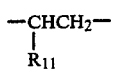

wherein $R_{11}$ is as defined above.

It is also contemplated that cyclic carbonate, XI, can be reacted directly with the hydroxy aliphatic acid, V, or preferably with the disodium salt thereof (dilithium or dipotassium salts are also contemplated) as shown in reaction (7) below:

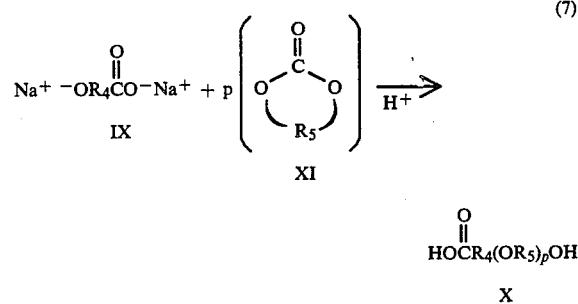

wherein $R_4$, $R_5$ and p are as defined above. The product, X, is then reacted with the polyamino alkenyl or alkyl succinimide as shown in reaction (5) above.

The preparation of hydrocarbyl-terminated products, i.e., $R_6$=hydrocarbyl of from 1 to 30 carbon atoms, can be accomplished by methods known in the art. In reaction (8) below the ester XIV is readily prepared:

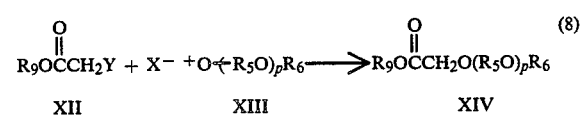

wherein $R_5$, $R_6$ and p are as defined above, $R_9$ is preferably lower alkyl of 1 to 4 carbon atoms; Y is chloro or bromo and X is sodium, potassium or lithium.

Reaction (8) is a displacement reaction to form the ethers, XIV. The reaction is generally conducted by adding equimolar amounts of XII to XIII. The reaction is generally conducted at from 0° to 110° C. and is generally complete from within 1 to 24 hours. The resulting ether-ester, XIV, may be isolated by conventional techniques, such as chromatography, filtration and the like.

The ether-ester, XIV, is then used directly in reaction (5) in place of the ether-acid, X, to form the products of this invention.

The halo-esters of XII above are either commercially available or can be readily prepared from the hydroxy aliphatic carboxylic acid. For example, reaction of the hydroxy aliphatic carboxylic acid with an alcohol, i.e., ethanol or methanol, under esterification conditions will yield the corresponding hydroxy aliphatic carboxylic acid ester. Reaction of this hydroxy aliphatic carboxylic acid ester with a halogenating agent, such as thionyl chloride or thionyl bromide, will yield the halo-ester, XII.

The hydrocarbyl capped poly(oxyalkylene) salts, XIII, are readily prepared from the hydrocarbyl capped poly(oxyalkylene) monool. Preparation of the hydrocarbyl capped poly(oxyalkylene) monool are described in U.S. Pat. No. 4,521,610 which is incorporated herein by reference for its teaching of the preparation of hydrocarbyl capped poly(oxyalkylene) monools, i.e., $R_6(OR_5)_pOH$.

Accordingly, by employing a polyamino alkenyl or alkyl succinimide of Formula II above in the processes of this invention, compounds of the following formula are produced:

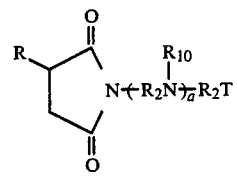

wherein R is alkenyl or alkyl of from 10 to 300 carbon atoms; $R_2$ is alkylene of from 2 to 10 carbon atoms; a is an integer of from 0 to 10 is selected from the group consisting of hydrogen, $C_1$-$C_6$ alkyl, $C_1$-$C_6$ hydroxyalkyl, $-R_5O)_pH$ wherein $R_5$ is alkylene of from 2 to 5 carbon atoms and p is an integer of from 1 to 100; and

wherein $R_4$ is alkylene of from 1 to 6 carbon atoms excluding $R_4$ groups wherein

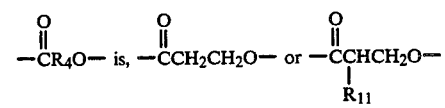

wherein $R_{11}$ is the remainder of the $R_4$ group, $R_5$ is alkylene of from 2 to 5 carbon atoms, m is an integer of from 0 to 2, and p is an integer of from 1 to 100; $R_6$ is selected from the group consisting hydrocarbyl of from 1 to 30 crbon atoms and hydrogen; T is selected from the group consisting of $-NHR_{10}$ and

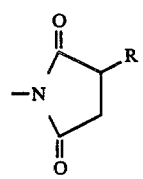

wherein R and $R_{10}$ are as defined above with the proviso that the compound contain at least one of $R_{10}$ which is

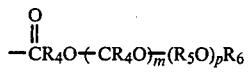

$$-CR_4O(CR_4O)_{\overline{m}}(R_5O)_pR_6$$

and with the further proviso that when m is 1 or 2 then $R_6$ is hydrogen and $R_{10}$ is not $-R_5O)_pH$.

R is preferably alkenyl or alkyl of from 20 to 300 carbon atoms and more preferably alkenyl or alkyl of from 20 to 100 carbon atoms.

$R_2$ is preferably alkylene of from 2 to 6 carbon atoms and a is preferably an integer of from 1 to 6.

Preferably, m is zero while $R_4$ is preferably alkylene of from 1 to 4 carbon atoms and more preferably alkylene of 1 carbon atom.

$R_5$ is preferably alkylene of from 2 to 4 carbon atoms while p is preferably an integer of from 1 to 30; more preferably, p is an integer of from 1 to 20; and most preferably, p is an integer of from 1 to 10.

$R_6$ is most preferably hydrogen.

The modified succinimides of this invention can be reacted at a temperature sufficient to cause reaction with boric acid or a similar boron compound to form borated dispersants having utility within the scope of this invention. In addition to boric acid (boron acid), examples of suitable boron compounds include boron oxides, boron halides and esters of boric acid. Generally from about 0.1 equivalents to 10 equivalents of boron compound to the modified succinimide may be employed.

The modified polyamino alkenyl or alkyl succinimides of this invention are useful as detergent and dispersant additives when employed in lubricating oils. When employed in this manner, the modified polyamino alkenyl or alkyl succinimide additive is usually present in from 0.2 to 10 percent by weight to the total composition and preferably at about 0.5 to 5 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. The concentrates of this invention usually include from about 90 to 10 weight percent of an oil of lubricating viscosity and from about 10 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

It is also contemplated the modified succinimides of this invention may be employed as dispersants and detergents in hydraulic fluids, marine crankcase lubricants and the like. When so employed, the modified succinimide is added at from about 0.1 to 10 percent by weight to the oil. Preferably, at from 0.5 to 5 weight percent.

When used in fuels, the proper concentration of the additive necessary in order to achieve the desired detergency is dependent upon a variety of factors including the type of fuel used, the presence of other detergents or dispersants or other additives, etc. Generally, however, and in the preferred embodiment, the range of concentration of the additive in the base fuel is 10 to 10,000 weight parts per million, preferably from 30 to 2,000 weight parts per million, and most preferably from 30 to 700 parts per million of the modified succinimide per part of base fuel. If other detergents are present, a lesser amount of the modified succinimide may be used.

The modified succinimide additives of this invention may be formulated as a fuel concentrate, using an inert stable oleophilic organic solvent boiling in the range of about 150° C. to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the fuel additive. In the fuel concentrate, the amount of the additive will be ordinarily at least 10 percent by weight and generally not exceed 70 percent by weight and preferably from 10 to 25 weight percent.

The following examples are offered to specifically illustrate this invention. These examples and illustrations are not to be construed in any way as limiting the scope of this invention.

EXAMPLES

EXAMPLE 1

Into a three-necked flask equipped with a mechanical stirrer and nitrogen sweep was added 486 g of a succinimide composition [prepared by reacting one mole of polyisobutenyl succinic anhydride, where the polyisobutenyl group has a number average molecular weight of about 950, with 0.5 mole of tetraethylene pentaamine, the diluting to about 50% actives in diluent oil; N=1.3% by weight, Alkalinity Value (AV)=26.5] and 15.2 g of 95% glycolic acid which contains about 5% water. The system was heated for three hours at 160° C. under a stream of nitrogen. Water distilled out. After cooling, 493 g of product was collected having an amide absorption in the Infrared Spectrum at 1660 cm$^{-1}$ and an AV=12.3.

EXAMPLE 2

To an autoclave was charged 361 g of a product prepared similarly to Example 1 above and 17.4 g (8.9 ml) of ethylene oxide. The autoclave was sealed and the mixture was heated at approximately 160° C. for three hours. The mixture was then allowed to cool and 346 g of product was collected having an AV=12.4 and having hydroxy, amide, ether and succinimide absorption in the Infrared Spectrum.

EXAMPLE 3

To a 500-ml reaction flask is charged 100 g of a product prepared similarly to example 1 above. The system is heated to 170° C. under N$_2$ and 9.64 g of ethylene carbonate is added. The reaction mixture is then stirred at 170° C. for four hours. The system is then cooled to yield a modified succinimide within the scope of this invention.

EXAMPLE 4

Into a three-necked flask equipped with a mechanical stirrer and nitrogen sweep was added 400 g of a succinimide composition [prepared by reacting one mole of polyisobutenyl succinic anhydride, where the polyisobutenyl group has a number average molecular weight of about 950, with 0.5 moles of tetraethylene pentaamine, then diluting to about 50% actives in diluent; n=1.51% by weight, Alkalinity Value (AV)=29.7] and 39.4 g of 95% glycolic acid which contains about 5% water. The system was heated for three hours at 160° C. under a stream of nitrogen. Water distilled out. After cooling, 428 g of product was collected having an AV=11.4; N=1.37% by weight and having amide and ester absorption in the Infrared Spectrum at 1660 cm$^{-1}$ and 1760 cm$^{-1}$, respectively.

EXAMPLE 5

To an autoclave was charged 298 g of the product of Example 4 and 98.5 g of ethylene oxide. The mixture was then heated at 160° C. for four hours. After cooling, 333 g of product was collected having an AV=11.9; N=1.22, and having hydroxy, amide, ester, ether and succinimide absorption in the Infrared Spectrum.

EXAMPLE 6

To a 500-ml reaction flask is charged 100 g of a product prepared similarly to Example 4 above. The system is heated to 170° C. under N$_2$ and 76 g of propylene carbonate is added. The reaction system is then stirred at 170° C. for four hours. The system is then cooled to yield a modified succinimide within the scope of this invention.

EXAMPLE 7

A. To a 2-liter reaction flask equipped with a mechanical stirrer and a nitrogen sweep is added 162 g of n-butoxy ethoxy ethanol (n-C$_4$H$_9$OCH$_2$CH$_2$OCH$_2$CH$_2$OH) and 500 ml of toluene. The system is stirred at room temperature and 23 g of metallic sodium is slowly added over a period of one hour to yield sodium n-butoxy ethoxy ethoxide (n-C$_4$H$_9$OCH$_2$CH$_2$OCH$_2$CH$_2$O$^-$Na$^+$).

To the toluene solution containing the sodium n-butoxy ethoxy ethoxide is added 122 g of ethylchloro acetate $$(ClCH_2\overset{O}{\overset{\|}{C}}OC_2H_5).$$

The system is then heated to 110° C. and stirred at this reaction temperature for four hours. Afterwards, the system is cooled and the toluene solution is washed twice with water, dried over anhydrous magnesium sulfate, filtered and stripped to yield ethyl n-butoxy ethoxy ethoxy acetate $$(\underline{n}\text{-}C_4H_9OCH_2CH_2OCH_2CH_2OCH_2\overset{O}{\overset{\|}{C}}OC_2H_5).$$

B. Into a three-necked flask equipped with a mechanical stirrer and nitrogen sweep is added 200 g of a succinimide composition [prepared by reacting one mole of polyisobutenyl succinic anhydride, where the polyisobutenyl group has a number average molecular weight of 950, with 0.87 moles of tetraethylene pentaamine, then diluting to about 50% actives in diluent oil] and 14.4 g of ethyl n-butoxy ethoxy ethoxy acetate. The system is heated for three hours at 160° C. under a stream of nitrogen. Afterwards, the system is stripped at elevated temperatures and reduced pressure to afford the n-butoxy ethoxy ethoxy acetamide $$(\underline{n}\text{-}C_4H_9OCH_2CH_2OCH_2CH_2OCH_2\overset{O}{\overset{\|}{C}}N\diagup_{\diagdown})$$

of the monosuccinimide.

What is claimed is:

1. A polyamino alkenyl or alkyl succinimide wherein one or more of the nitrogens of the polyamino moiety is substituted with:

$$-\overset{O}{\overset{\|}{C}}R_4O\text{-}(\overset{O}{\overset{\|}{C}}R_4O)_{\overline{m}}(R_5O)_{\overline{p}}R_6$$

wherein R$_4$ is alkylene of from 1 to 6 carbon atoms excluding R$_4$ groups wherein $$-\overset{O}{\overset{\|}{C}}R_4O- \text{ is } -\overset{O}{\overset{\|}{C}}CH_2CH_2O- \text{ and } -\overset{O}{\overset{\|}{C}}CHCH_2O-\\ \phantom{xxxxxxxxxxxxxxxxxxxxxxxxxxxxxxxxxx}|\\ \phantom{xxxxxxxxxxxxxxxxxxxxxxxxxxxxxxxxxx}R_{11}$$

wherein R$_{11}$ is the remainder of the R$_4$ group; m is an integer of from 0 to 2; R$_5$ is alkylene of from 2 to 5 carbon atoms; p is an integer of from 1 to 100; R$_6$ is selected from the group consisting of hydrogen and hydrocarbyl of from 1 to 30 carbon atoms; and with the proviso that if m is one or two then R$_6$ is hydrogen.

2. The polyamino alkenyl or alkyl succinimide as defined in claim 1 wherein the alkenyl or alkyl group is from about 20 to 300 carbon atoms.

3. The polyamino alkenyl or alkyl succinimide as defined in claim 2 wherein m is zero and R$_6$ is hydrogen.

4. The polyamino alkenyl or alkyl succinimide as defined in claim 3 wherein p is an integer of from 1 to 30.

5. The polyamino alkenyl or alkyl succinimide as defined in claim 4 wherein $R_4$ is alkylene of from 1 to 4 carbon atoms.

6. The polyamino alkenyl or alkyl succinimide as defined in claim 5 wherein $R_5$ is alkylene of from 2 to 4 carbon atoms.

7. A compound of the formula

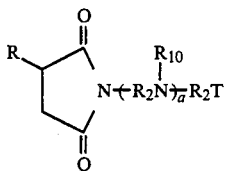

wherein R is alkenyl or alkyl of from 10 to 300 carbon atoms; $R_2$ is alkylene of from 2 to 10 carbon atoms; a is an integer from 0 to 10; $R_{10}$ is selected from the group consisting of hydrogen, $C_1$-$C_6$ alkyl, $C_1$-$C_6$ hydroxyalkyl, $-R_5O)_pH$ wherein $R_5$ is alkylene of from 2 to 5 carbon atoms and p is an integer of from 1 to 100, and

wherein $R_4$ is alkylene of from 1 to 6 carbon atoms excluding $R_4$ groups wherein

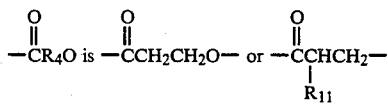

wherein $R_{11}$ is the remainder of the $R_4$ group, $R_5$ is alkylene of from 2 to 5 carbon atoms, m is an integer of from 0 to 2, and p is an integer of from 1 to 100, $R_6$ is selected from the group consisting of hydrocarbyl of from 1 to 30 carbon atoms and hydrogen; T is selected from the group consisting of $-NHR_{10}$ and

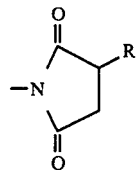

wherein R and $R_{10}$ are as defined above with the proviso that the compound contain at least one of $R_{10}$ which is

and with the further proviso that when m is 1 or 2, then $R_6$ is hydrogen and $R_{10}$ is not $-R_5O)_pH$.

8. A compound of the formula as defined in claim 7 wherein R is alkenyl or alkyl of from 20 to 300 carbon atoms.

9. A compound of the formula as defined in claim 8 wherein a is an integer of from 1 to 6 and $R_2$ is alkylene of from 2 to 6 carbon atoms.

10. A compound of the formula as defined in claim 8 wherein m is zero and $R_6$ is hydrogen.

11. A compound of the formula as defined in claim 10 wherein p is an integer of from 1 to 30 and $R_5$ is alkylene of from 2 to 4 carbon atoms.

12. A compound of the formula as defined in claim 11 wherein $R_4$ is alkylene of from 1 to 4 carbon atoms.

13. A lubricating oil composition comprising an oil of lubricating viscosity and a dispersant effective amount of a compound as defined in claim 1.

14. A lubricating oil composition comprising an oil of lubricating viscosity and a dispersant effective amount of a compound as defined in claim 7.

15. A lubricating oil concentrate comprising from about 10 to 90 weight percent of an oil of lubricating viscosity and from about 90 to 10 weight percent of a compound as defined in claim 1.

16. A lubricating oil concentrate comprising from about 10 to 90 weight percent of an oil of lubricating viscosity and from about 90 to 10 weight percent of a compound as defined in claim 7.

* * * * *

UNITED STATES PATENT AND TRADEMARK OFFICE
CERTIFICATE OF CORRECTION

PATENT NO. : 4,680,129
DATED : July 14, 1987
INVENTOR(S) : Frank Plavac and Robert H. Wollenberg It is certified that error appears in the above-identified patent and that said Letters Patent are hereby corrected as shown below:

Cover page, "Plavac" should read -- Plavac et al --.

Cover page, "Inventor: Frank Plavac, Novato, Calif." should read -- Frank Plavac, Novato, Calif. and Robert H. Wollenberg, San Rafael, Calif. --.

Signed and Sealed this

Seventeenth Day of November, 1987

Attest:

DONALD J. QUIGG

*Attesting Officer*

*Commissioner of Patents and Trademarks*

UNITED STATES PATENT AND TRADEMARK OFFICE
CERTIFICATE OF CORRECTION

PATENT NO. : 4,680,129

DATED : July 14, 1987

INVENTOR(S) : Frank Plavac et al.

It is certified that error appears in the above-identified patent and that said Letters Patent are hereby corrected as shown below:

Col. 8, lines 47-50, "p $\overset{O}{R_5}$" should read --p $\left(\overset{O}{\underset{R_5}{\frown}}\right)$ --.

Col. 11, line 4, "-R$_5$O)$_p$H" should read --$($R$_5$O$)_p$H--.

Col. 11, line 33, " →Na$^+$ $^-$OR$_4$$\overset{O}{C}$O-Na$^{+}$" should read

-- →Na$^+$ $^-$OR$_4\overset{O}{\overset{\|}{C}}$O$^-$Na$^+$ --.

Col. 11, line 37, "p $\overset{O}{R_5}$" should read --p $\left(\overset{O}{\underset{R_5}{\frown}}\right)$--.

Col. 17, line 7, "-R$_5$O)$_p$H" should read --$($R$_5$O$)_p$H --.

UNITED STATES PATENT AND TRADEMARK OFFICE
CERTIFICATE OF CORRECTION

PATENT NO. : 4,680,129
DATED : July 14, 1987
INVENTOR(S) : Frank Plavac et al.

It is certified that error appears in the above-identified patent and that said Letters Patent are hereby corrected as shown below:

Claim 7, Col. 21, line 26, "$-R_5O)_pH$" should read

--$(R_5O)_pH$--

Claim 7, Col. 22, line 19, "$-R_5O)_pH$" should read

--$(R_5O)_pH$--

Signed and Sealed this

Fifth Day of January, 1988

Attest:

DONALD J. QUIGG

Attesting Officer     Commissioner of Patents and Trademarks